United States Patent
Garneyer et al.

(10) Patent No.: US 10,481,066 B2
(45) Date of Patent: Nov. 19, 2019

(54) SOOT SENSOR

(71) Applicant: Continental Automotive GmbH, Hannover (DE)

(72) Inventors: Eckart Garneyer, Regensburg (DE); Sebastian Reiss, Lappersdorf (DE); Patrick Eber-Neumaier, Altfraunhofen (DE); Alexander Waha, Lappersdorf (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 0 days.

(21) Appl. No.: 15/525,692

(22) PCT Filed: Nov. 10, 2015

(86) PCT No.: PCT/EP2015/076183
§ 371 (c)(1),
(2) Date: May 10, 2017

(87) PCT Pub. No.: WO2016/075127
PCT Pub. Date: May 19, 2016

(65) Prior Publication Data
US 2017/0315043 A1    Nov. 2, 2017

(30) Foreign Application Priority Data
Nov. 10, 2014   (DE) .................. 10 2014 222 844

(51) Int. Cl.
*G01N 15/06* (2006.01)
*F01N 11/00* (2006.01)
(Continued)

(52) U.S. Cl.
CPC ....... *G01N 15/0656* (2013.01); *F01N 11/007* (2013.01); *G01N 27/60* (2013.01); *F01N 2560/05* (2013.01); *G01N 2015/0046* (2013.01)

(58) Field of Classification Search
CPC .............. G01N 15/0656; G01N 27/60; G01N 2015/0046; F01N 11/007; F01N 2560/05
See application file for complete search history.

(56) References Cited

U.S. PATENT DOCUMENTS

| | | | |
|---|---|---|---|
| 7,872,466 B2 * | 1/2011 | Dorfmueller | G01N 15/0656 324/515 |
| 2004/0260166 A1 * | 12/2004 | Merilainen | A61B 5/04085 600/383 |

(Continued)

FOREIGN PATENT DOCUMENTS

| | | | |
|---|---|---|---|
| DE | 2445004 A1 | 4/1976 | ............. F02D 41/14 |
| DE | 19536705 A1 | 4/1997 | ............... F01N 3/01 |

(Continued)

OTHER PUBLICATIONS

DE 12004059650 A1 U.S. Pat. No. 7,872,466 B2.
(Continued)

*Primary Examiner* — Huy Q Phan
*Assistant Examiner* — Zannatul Ferdous
(74) *Attorney, Agent, or Firm* — Slayden Grubert Beard PLLC

(57) ABSTRACT

The present disclosure relates to exhaust gas emissions in motor vehicles. The teachings thereof may be embodied in soot sensors. For example, a soot sensor may include: a first electrode; a second electrode; an insulation body between the first electrode and the second electrode configured to allow soot particles to pass with a gas flow into a space defined between the first electrode and the second electrode; a meter evaluating a current between the first electrode and (Continued)

the second electrode resulting from an electrical voltage applied between the first electrode and the second electrode; and elements concentrating the electric field strength formed on at least one of a surface of the first electrode or a surface of the second electrode.

7 Claims, 3 Drawing Sheets

(51) Int. Cl.
*G01N 27/60* (2006.01)
*G01N 15/00* (2006.01)

(56) References Cited

U.S. PATENT DOCUMENTS

| | | | | |
|---|---|---|---|---|
| 2005/0068617 | A1* | 3/2005 | Mizuno | G03B 21/56 359/443 |
| 2006/0070889 | A1* | 4/2006 | Ehrismann | G01N 27/301 205/775 |
| 2007/0069263 | A1* | 3/2007 | Mizuuchi | G11C 11/22 257/295 |
| 2009/0056416 | A1* | 3/2009 | Nair | G01N 15/0656 73/28.01 |
| 2011/0003279 | A1* | 1/2011 | Patel | G01D 3/10 435/5 |
| 2011/0314796 | A1* | 12/2011 | Nakamura | F01N 9/002 60/276 |
| 2011/0314899 | A1* | 12/2011 | Di Miro | F02D 41/1466 73/23.33 |
| 2012/0062254 | A1* | 3/2012 | Wienand | G01N 15/0656 324/691 |
| 2013/0000386 | A1 | 1/2013 | Korenev | 73/31.05 |
| 2013/0283887 | A1* | 10/2013 | Ante | F01N 9/002 73/28.01 |
| 2014/0165979 | A1* | 6/2014 | Nishijima | F01N 9/002 123/672 |
| 2016/0195464 | A1* | 7/2016 | Trautmann | G01N 15/0656 73/28.01 |
| 2017/0226646 | A1* | 8/2017 | Nourbakhsh | C25B 1/26 |

FOREIGN PATENT DOCUMENTS

| | | | | |
|---|---|---|---|---|
| DE | 19853841 | A1 | 6/1999 | G01M 15/10 |
| DE | 19817402 | C1 | 9/1999 | G01N 27/62 |
| DE | 10128869 | A1 | 1/2002 | G01N 27/22 |
| DE | 102004039647 | A1 | 2/2006 | G01N 15/06 |
| DE | 102004059650 | A1 | 6/2006 | G01N 27/04 |
| DE | 102006040351 | A1 | 3/2008 | G01N 27/04 |
| DE | 102007033213 | A1 | 1/2009 | G01N 27/02 |
| WO | 2016/075127 | A1 | 5/1916 | G01N 15/06 |

OTHER PUBLICATIONS

German Office Action, Application No. 102014222844.1, 7 pages, dated Jun. 25, 2015.
International Search Report and Written Opinion, Application No. PCT/EP2015/076183, 23 pages, dated Feb. 4, 2016.
Chinese Office Action, Application No. 201580061153.X, 17 pages, dated Jan. 17, 2019.

* cited by examiner

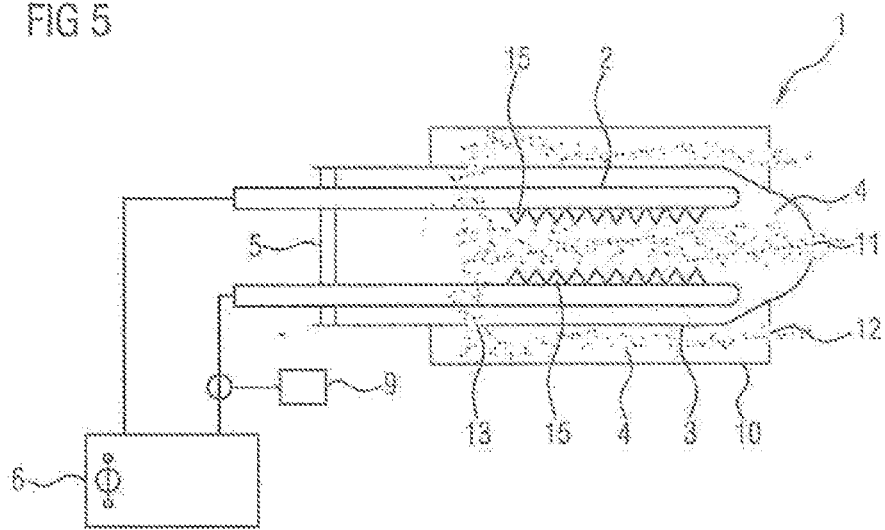

SOOT SENSOR

CROSS-REFERENCE TO RELATED APPLICATIONS

This application is a U.S. National Stage Application of International Application No. PCT/EP2015/076183 filed Nov. 10, 2015, which designates the United States of America, and claims priority to DE Application No. 10 2014 222 844.1 filed Nov. 10, 2014, the contents of which are hereby incorporated by reference in their entirety.

TECHNICAL FIELD

The present disclosure relates to exhaust gas emissions in motor vehicles. The teachings thereof may be embodied in soot sensors.

BACKGROUND

The reduction of exhaust-gas emissions in motor vehicles is an important aim in the development of new motor vehicles. Therefore, combustion processes in internal combustion engines are thermodynamically optimized such that the efficiency of the internal combustion engine is considerably improved. In the automotive sector, increasing use is being made of diesel engines which, in modern embodiments, exhibit very high efficiency. One disadvantage of diesel engines in relation to optimized Otto-cycle engines may be increased soot emissions. Soot may be particularly carcinogenic owing to the concentration of polycyclic aromatic compounds; various regulations have already been introduced in response to this concern. For example, exhaust-gas emissions standards with maximum limits for soot emissions have been enacted.

Compliance with the exhaust-gas emissions standards for motor vehicles with diesel engines relies on sensors which measure the soot content in the exhaust-gas flow of the motor vehicle.

Such soot sensors measure the soot being emitted, to provide the engine management system in a motor vehicle, in a present driving situation, with information enabling it to reduce the emissions values using regulation-based adaptations. Furthermore, by means of the soot sensors, active exhaust-gas purification by means of exhaust-gas soot filters may be initiated, or for exhaust-gas recirculation to the internal combustion engine may be implemented. In the case of soot filtering, regeneratable filters are used which filter out a major part of the soot content from the exhaust gas. Soot sensors monitor the function of the soot filters and control the regeneration cycles thereof. A soot sensor may be positioned upstream and/or downstream of the soot filter, which is also referred to as diesel particle filter.

A sensor positioned upstream of the diesel particle filter increases the system reliability and ensures operation of the diesel particle filter under optimum conditions. Since this is highly dependent on the soot quantity stored in the diesel particle filter, accurate measurement of the particle concentration upstream of the diesel particle filter system, e.g., the determination of a high particle concentration upstream of the diesel particle filter, is of high importance. A soot sensor positioned downstream of the diesel particle filter enables vehicle-internal diagnostics and ensures correct operation of the exhaust-gas aftertreatment system.

The prior art presents various approaches for the detection of soot. An approach widely implemented in laboratories consists in using the light scatter through the soot particles. This approach uses cumbersome measurement apparatuses. To implement this as a mobile sensor system in the exhaust tract, use of an optical sensor in a motor vehicle is associated with very high costs. Furthermore, unresolved problems exist with regard to the fouling of the required optical window with combustion exhaust gases.

DE 195 36 705 A1 discloses a device for measuring soot particles, wherein an electric field is generated by means of the application of a constant electrical direct-current voltage between a casing electrode through which the gas flow passes and an inner electrode within said casing electrode, and the charge current for maintaining the constant direct-current voltage between casing electrode and inner electrode is measured. Good measurement results are obtained, in the context of the disclosure of DE 195 36 705 A1, if a direct-current voltage of 2000 to 3000 volts is used to generate the electric field. In the case of these electrostatic soot sensors, the current between the two electrodes changes in a manner dependent on the soot concentration in the exhaust-gas flow. The currents that arise here are however relatively small, and the current intensity thereof lies in the range from pA to low nA values. Therefore, the entire measurement arrangement for said electrostatic soot sensors must be of very high-impedance design.

SUMMARY

The teachings of the present disclosure may provide a soot sensor with a considerably higher measurement current. For example, a soot sensor (1) may have a first electrode (2) and a second electrode (3), wherein the first electrode (2) and the second electrode (3) are electrically insulated with respect to one another by means of an insulation body (5) and an electrical voltage can be applied between the first electrode (2) and the second electrode (3), wherein soot particles (4) can pass with a gas flow into the space between the first electrode (2) and the second electrode (3), characterized in that elements (15) for concentrating the electric field strength are formed on the surface of the first electrode (2) and/or on the surface of the second electrode (3).

In some embodiments, the first electrode (2) is of rod-shaped form.

In some embodiments, the second electrode (3) is of cylindrical form.

In some embodiments, the cylindrical second electrode (3) is formed concentrically around the rod-shaped first electrode (2).

In some embodiments, the elements (15) for concentrating the electric field strength are in the form of spike-like tips.

In some embodiments, the elements (15) for concentrating the electric field strength are in the form of triangular tips.

In some embodiments, the elements (15) for concentrating the electric field strength are in the form of grooves in the surface of the first electrode (2) and/or in the surface of the second electrode (3).

In some embodiments, the elements (15) for concentrating the electric field strength are formed by nanostructuring of the surface of the first electrode (2) and/or of the surface of the second electrode (3).

BRIEF DESCRIPTION OF THE DRAWINGS

Below, the teachings of the present disclosure will be discussed with reference to the appended drawings and on the basis of illustrated embodiments. Said embodiments comprise soot sensors for use in a motor vehicle. In the drawings:

FIG. 5 shows a further embodiment of the soot sensor according to the teachings of the present disclosure.

DETAILED DESCRIPTION

Because elements for concentrating the electric field strength are formed on the surface of the first electrode and/or on the surface of the second electrode, it is possible with a relatively low voltage to generate a high measurement current between the first electrode and the second electrode, which measurement current is proportional to the number of soot particles in the exhaust gas.

In some embodiments, the first electrode is of rod-shaped form. This shape makes it possible to produce a very compact soot sensor. If the second electrode is of cylindrical form, a soot sensor can be produced in the case of which the cylindrical second electrode is formed concentrically around the rod-shaped first electrode. The soot sensor thus created has a long service life and a very compact design.

In some embodiments, the elements for concentrating the electric field strength are in the form of spike-like tips. Spike-like tips make it possible to realize a very high concentration of the electric field, whereby it is possible in a very small space to achieve high field strengths, which can lead to avalanche-like intensifications of the charge carriers between the first electrode and the second electrode.

If the elements for concentrating the electric field strength are in the form of triangular tips, it is possible to realize a very durable soot sensor, because the triangular tips are very robust components.

In some embodiments, the elements for concentrating the electric field strength are in the form of grooves in the surface of the first electrode and/or in the surface of the second electrode. Grooves can be produced particularly easily in a surface and are thus particularly inexpensive.

If the elements for concentrating the electric field strength are formed by nanostructuring of the surface of the first electrode and/or of the surface of the second electrode, the electric fields and the electric field strengths associated therewith can be particularly easily predetermined and properly modeled, which leads to a soot sensor with particularly accurate measurement capabilities.

Figure 1:
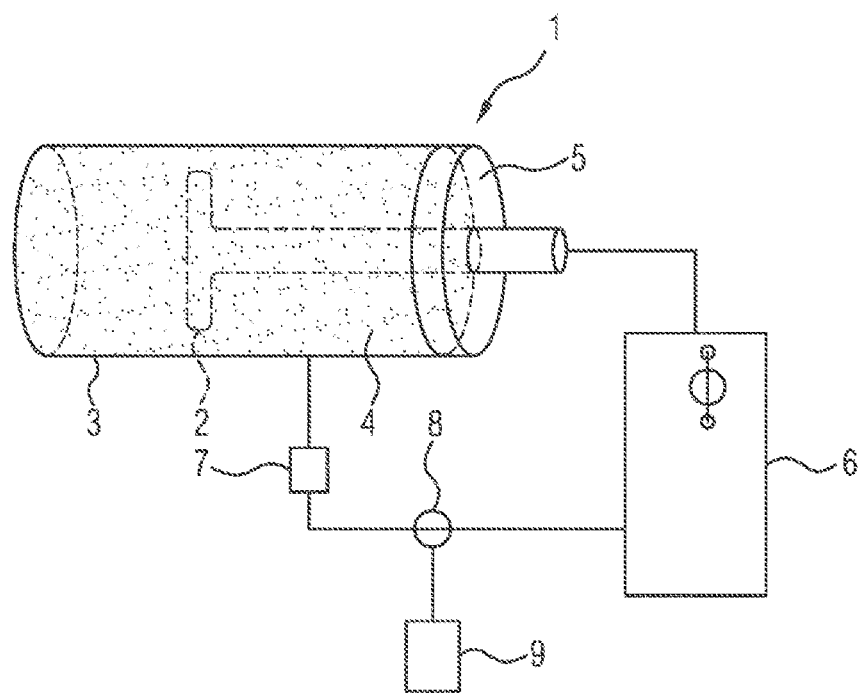
FIG. 1 shows a soot sensor.

FIG. 1 shows a known soot sensor 1. The soot sensor 1 is composed of a first electrode 2, which is arranged in the interior of a second electrode 3. The exhaust gas, which contains soot particles 4, of the internal combustion engine is situated between the first electrode 2 and the second electrode. It is sought to measure the concentration of the soot particles 4 in the exhaust gas by means of the soot sensor. For this purpose, a measurement voltage is applied between the first electrode 2 and the second electrode 3 by the voltage supply 6. The first electrode 2 is electrically insulated with respect to the second electrode 3 by means of the insulation body 5. The insulation body 5 may be constructed as a disk composed of a ceramic material. Furthermore, it can be seen in FIG. 1 that an ohmic resistance 7 is connected between the voltage supply and the second electrode 3, which ohmic resistance exhibits high impedance in order to measure the relatively small currents that can form between the first electrode 2 and the second electrode 3 owing to the soot particles 4. The measurement of said currents is realized by means of the current measurement element 8, which is connected to evaluation electronics 9. Such soot sensors 1 are used for on-board diagnosis in motor vehicles with diesel engines.

The voltage that must be applied between the first electrode 2 and the second electrode 3 in order to obtain evaluable measurement currents is relatively high. Such a voltage may amount to 2 to 3 kV and is thus relatively cumbersome to monitor. It is therefore advantageous, in order to generate easily evaluable measurement currents, to use the embodiments of the first electrode 2 and/or of the second electrode 3, as described below.

Figure 2:
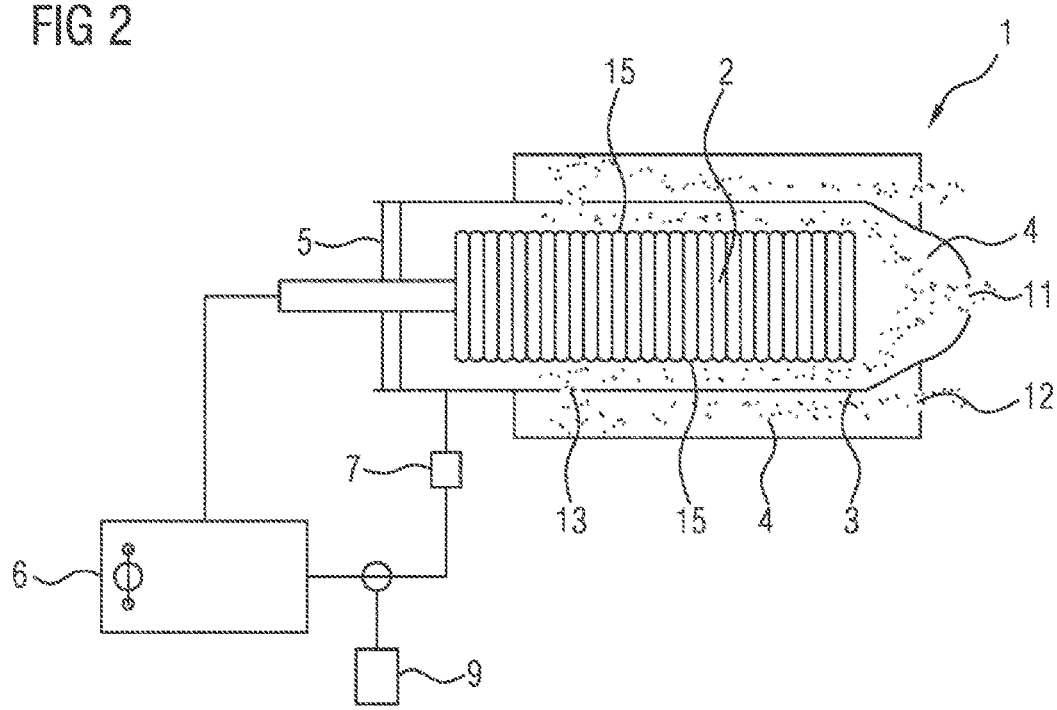
FIG. 2 shows a soot sensor according to the teachings of the present disclosure.

FIG. 2 shows a soot sensor 1 according to the teachings of the present disclosure with a first electrode 2 and a second electrode 3. The first electrode 2 is electrically insulated with respect to the second electrode 3 by means of an insulation body 5, and an electrical voltage, which is generated by the electrical voltage supply 6, is applied between the first electrode 2 and the second electrode 3.

Soot particles 4 which are transported in an exhaust-gas flow from an internal combustion engine through an exhaust tail pipe can enter the soot sensor 1 which may be integrated in the exhaust tail pipe. The soot particles 4 pass into an electric field which forms owing to the electrical voltage applied between the first electrode 2 and the second electrode 3.

To generate a more easily measurable electrical current between the first electrode 2 and the second electrode 3, elements 15 for concentrating the electric field strength are formed on the surface of the first electrode 2 and/or on the surface of the second electrode 3. In this example, the first electrode 2 comprises a rod-shaped threaded bar, wherein the elements 15 for concentrating the electric field strength are formed by the thread flights, between which triangular tips are formed.

The electric field is concentrated at these tips and the electric field strength becomes very high in the region of the tips. The intense increase in the electric field strength in the region of the tips can exceed the breakdown field strength of the gas in said region. In the event of the breakdown field strength of the gas being exceeded, electrically charged particles are formed which are accelerated in the direction of the opposite electrode and, owing to impact ionization events, lead to an avalanche-like formation of charge carriers. When said charge carrier avalanche reaches an electrode surface, a very high current can be measured, which can be easily evaluated and which is proportional to the number of charged particles in the exhaust gas.

FIG. 2 however also shows an ohmic resistance 7, which may be used to measure, by means of the evaluation electronics 9, the electrical current that flows between the first electrode 2 and the second electrode 3. FIG. 2 shows a protective cap 10 which serves for the targeted guidance of the exhaust-gas flow through the soot sensor 1. The exhaust gases may enter the soot sensor 1 through a first opening 11, where the soot content in the exhaust gas can be measured between the first electrode 2 and the second electrode 3. Thereafter, the exhaust-gas flow exits the soot sensor 1 through the second opening 12 formed in the second electrode 3, and is conducted back into the main exhaust-gas flow via the third opening 13.

Figure 3:
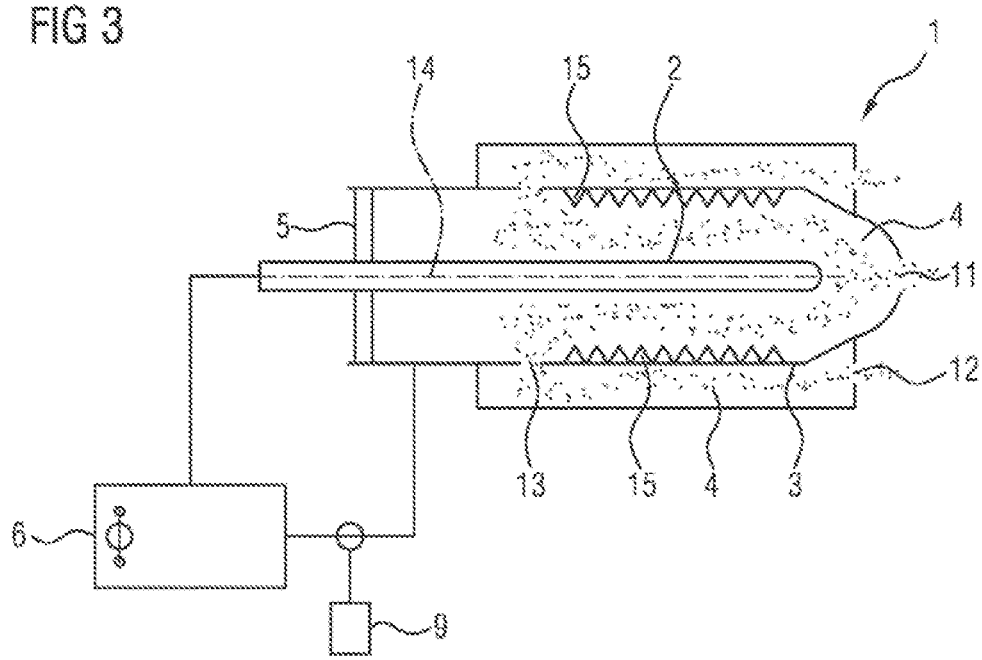
FIG. 3 shows a further embodiment of the soot sensor according to the teachings of the present disclosure.

FIG. 3 shows a further embodiment of the soot sensor 1 according to teachings of the present disclosure. Here, the soot sensor 1 is of rotationally symmetrical form about a central axis 14. The first electrode 2 comprises a rod-shaped electrode. The cylindrical second electrode 3 is formed concentrically around the second electrode. The second electrode 3 comprises a hollow cylinder. The insulation body 5, which in this case is in the form of a disk, electrically separates the first electrode 2 from the second electrode 3. A voltage can be applied between the first electrode 2 and the second electrode 3 by means of the voltage supply 6.

The elements 15 for field concentration formed on the inner surface of the second electrode 3 comprise triangles. The tips of the triangles lead to a very high field strength in the region of the tips of the triangles. Owing to said high field strength, the breakdown field strength in the exhaust gas can be exceeded, whereby, owing to avalanche-like impact ionization, a high measurement current can be generated, which can be easily registered by means of the evaluation electronics 9.

Figure 4:
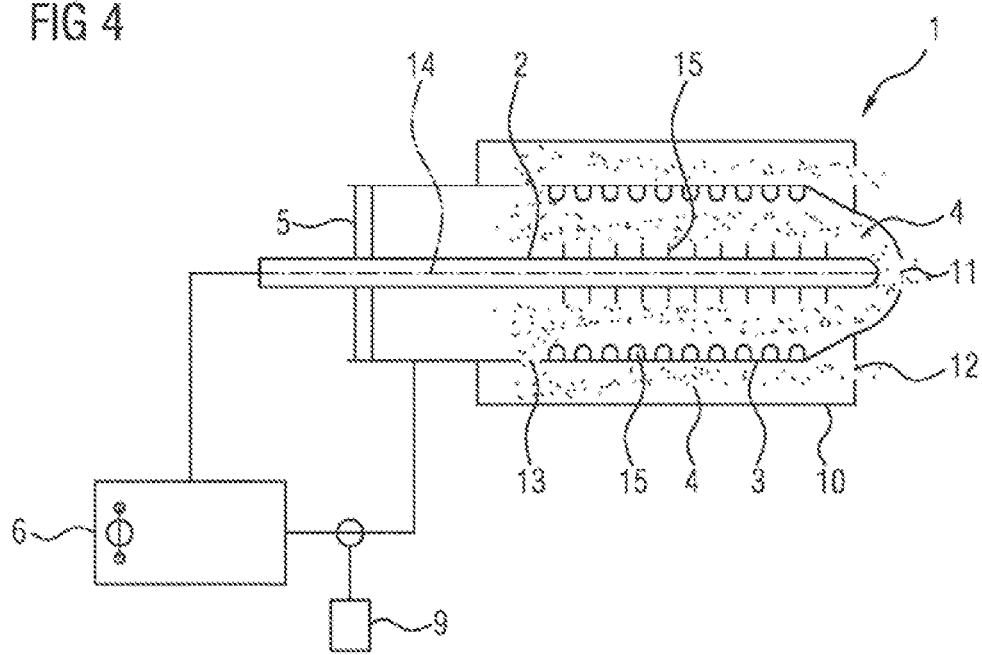
FIG. 4 shows a further embodiment of the soot sensor known from FIG. 3.

FIG. 4 shows a further embodiment of the soot sensor 1 from FIG. 3. The first electrode 2 includes elements 15 for concentrating the electric field strength, which elements are in the form of spike-like tips. The second electrode 3, on its inner surface, has semicircular elements 15 for concentrating the electric field strength. A multiplicity of possible surface structures of the first electrode 2 and of the second electrode 3 are conceivable, whereby targeted modeling of the field distribution in the interior of the soot sensor 1 is possible.

FIG. 5 shows a further embodiment of the soot sensor 1 according to teachings of the present disclosure. Here, both the first electrode 2 and the second electrode 3 comprise rod-shaped elements. Triangular elements 15 for concentrating the electric field strength are formed both on the first electrode 2 and the second electrode 3. The first electrode 2 and the second electrode 3 are electrically insulated with respect to one another by means of the insulation body 5. A protective cap 10 is formed over the first electrode 2 and over the second electrode 3. The protective cap 10 again, by means of the first opening 11, the second opening 12, and the third opening 13, allows the exhaust gas and the soot particles to flow into the interior of the soot sensor 1 and thus also between the first electrode 2 and a second electrode 3. The second electrode 3 may comprise a hollow cylinder.

What is claimed is:

1. A soot sensor comprising:
   a first electrode;
   a second electrode defining an internal cavity having a longitudinal extent and radially surrounded by material of the second electrode;
   wherein the first electrode is disposed at least partially within the internal cavity of the second electrode;
   an insulation body electrically separating the first electrode and the second electrode from one another, the insulation body in physical contact with both the first electrode and the second electrode, projecting into the internal cavity, and configured to allow soot particles to pass with a gas flow into the internal cavity between the first electrode and the second electrode;
   a meter evaluating a current between the first electrode and the second electrode resulting from an electrical voltage applied between the first electrode and the second electrode; and
   elements concentrating the electric field strength formed on at least one of a surface of the first electrode or a surface of the second electrode.

2. The soot sensor as claimed in claim 1, wherein the first electrode comprises a rod shape.

3. The soot sensor as claimed in claim 1, wherein the second electrode comprises a cylindrical shape.

4. The soot sensor as claimed in claim 2, wherein the second electrode comprises a cylindrical shape arranged concentrically around the rod-shaped first electrode.

5. The soot sensor as claimed in claim 1, wherein the elements comprise spike-like tips.

6. The soot sensor as claimed in claim 1, wherein the elements comprise triangular tips.

7. The soot sensor as claimed in claim 1, wherein the elements comprise nanostructures on the surface of the first electrode or the surface of the second electrode.

* * * * *